(12) United States Patent
Cocchi et al.

(10) Patent No.: US 10,676,774 B2
(45) Date of Patent: Jun. 9, 2020

(54) APPARATUS AND METHOD FOR DETERMINING THE BACTERIAL CHARGE IN A LIQUID OR SEMI-LIQUID PRODUCT

(71) Applicant: ALI GROUP S.r.l.—CARPIGIANI, Cernusco sul Naviglio (Milan) (IT)

(72) Inventors: Andrea Cocchi, Calderara di Reno (IT); Roberto Lazzarini, Reggio Emilia (IT)

(73) Assignee: ALI GROUP S.R.L.—CARPIGIANI, Cernuscu Sul (IT)

(*) Notice: Subject to any disclaimer, the term of this patent is extended or adjusted under 35 U.S.C. 154(b) by 0 days.

(21) Appl. No.: 15/947,170

(22) Filed: Apr. 6, 2018

(65) Prior Publication Data

US 2018/0305729 A1    Oct. 25, 2018

(30) Foreign Application Priority Data

Apr. 21, 2017  (IT) .................. 102017441 03

(51) Int. Cl.

| | |
|---|---|
| *C12Q 1/04* | (2006.01) |
| *G01N 27/02* | (2006.01) |
| *C12M 1/34* | (2006.01) |
| *G01N 33/487* | (2006.01) |
| *G01N 33/18* | (2006.01) |
| *G01N 33/04* | (2006.01) |

(52) U.S. Cl.
CPC ............. *C12Q 1/04* (2013.01); *G01N 27/02* (2013.01); *G01N 27/026* (2013.01); *G01N 33/04* (2013.01); *G01N 33/1826* (2013.01); *G01N 33/48707* (2013.01); *G01N 33/48735* (2013.01); *C12M 41/36* (2013.01)

(58) Field of Classification Search
CPC ................... G01N 27/02; C12Q 1/04

USPC ........................................ 435/287.1
See application file for complete search history.

(56) References Cited

U.S. PATENT DOCUMENTS

| | | | |
|---|---|---|---|
| 2013/0094998 A1* | 4/2013 | Roth ...................... | G01N 27/07 422/73 |
| 2014/0044841 A1* | 2/2014 | Luckhardt ............ | A23B 4/0053 426/233 |
| 2016/0348056 A1* | 12/2016 | Parikh ..................... | C12M 41/26 |

FOREIGN PATENT DOCUMENTS

WO    WO2013123189 A1    8/2013

OTHER PUBLICATIONS

Grossi et al., A Portable Sensor With Disposable Electrodes for Water Bacterial Quality Assessment, May 2013, IEE Sensors Journal, vol. 13, pp. 1775-1782 (Year: 2013).*

(Continued)

*Primary Examiner* — Kevin Joyner
*Assistant Examiner* — Holly Kipouros
(74) *Attorney, Agent, or Firm* — Shuttleworth & Ingersoll, PLC; Timothy J. Klima (57) ABSTRACT

A method for determining the bacterial charge in a liquid or semi-liquid product, including: preparing a quantity of liquid or semi-liquid product to be analyzed; keeping that quantity of liquid or semi-liquid product at a preset measuring temperature ($T_m$) and deriving values ($\alpha$) representing an angle of electrical impedance of the liquid or semi-liquid product at predetermined time instants; deriving an indication of the presence of a bacterial charge in the liquid or semi-liquid product as a function of the time trend of the values ($\alpha$) representing the angle of the electrical impedance.

16 Claims, 4 Drawing Sheets

(56) References Cited

OTHER PUBLICATIONS

Xie, An electrochemical impedance spectroscopy based nitrate sensor for practical application, Jun. 2016, Massey University, pp. 1-87 (Year: 2016).*
Chen et al., Fast and sensitive detection of foodborne pathogen using electrochemical impedance analysis, urease catalysis and microfluidics, Jul. 2016, Biosensors & Bioelectronics, vol. 86, pp. 770-776 (Year: 2016).*
Italian Search Report dated Dec. 1, 2017 for counterpart Italian Patent Application No. IT2017000044103.
Grossi et al, "An embedded portable biosensor system for bacterial concentration detection", Biosensors and Bioelectronics, Elsevier BV, NL, vol. 26, No. 3, Nov. 15, 2010, pp. 983-990.
Chen et al, "A dielectric loss angle based portable biosensor system for bacterial concentration detection", RSC Advances, vol. 5, No. 104, Jan. 1, 2015, pp. 85919-85927.

* cited by examiner

APPARATUS AND METHOD FOR DETERMINING THE BACTERIAL CHARGE IN A LIQUID OR SEMI-LIQUID PRODUCT

This application claims priority to Italian Patent Application 102017000044103 filed Apr. 21, 2017, the entirety of which is incorporated by reference herein.

BACKGROUND OF THE INVENTION

This invention relates to an apparatus and a method for determining the bacterial charge in a liquid or semi-liquid food product, in particular in a milk and/or water based food mixture.

The considerable importance of determining and checking the bacterial charge and/or the microbial content in liquid or semi-liquid food products is well known because these products are intended for consumption as foodstuffs.

Indeed, excessively high microbial concentrations (if pathogenic) can constitute a serious threat to human health.

A need which is felt particularly strongly in the food sector, therefore, is that of being able to measure in an extremely simple and reliable manner, the quantity of bacterial charge in liquid or semi-liquid food products directly on the spot, that is, at the place of production.

Another need which is felt particularly strongly in the food sector, therefore, is that of being able to measure the quantity of bacterial charge in a quick and inexpensive way.

SUMMARY OF THE INVENTION

This invention therefore has for an arm to meet the above mentioned needs by providing an apparatus and a method for determining the bacterial charge in a liquid or semi-liquid food product.

More specifically, the aim of this invention is to provide an apparatus and a method for determining the bacterial charge in a liquid or semi-liquid food product in an extremely simple and reliable way.

Another aim of this invention is to provide an apparatus and a method for determining the bacterial charge in a liquid or semi-liquid food product in a quick and inexpensive way.

These and other aims are substantially achieved by the apparatus and method for determining the bacterial charge in a liquid or semi-liquid product as described in the accompanying claims.

Further features and advantages are more apparent from the detailed description of a preferred, hence non-limiting, example embodiment of the invention.

BRIEF DESCRIPTION OF THE DRAWINGS

The technical features of the invention, with reference to the above aims, are clearly described in the claims below and its advantages are more apparent from the detailed description which follows, with reference to the accompanying drawings which illustrate a non-limiting example embodiment of the invention, and in which:

DESCRIPTION OF THE PREFERRED EMBODIMENTS

With reference to the accompanying drawings, the numeral 1 denotes an apparatus for determining the bacterial charge in liquid or semi-liquid products according to the invention.

Figure 1:
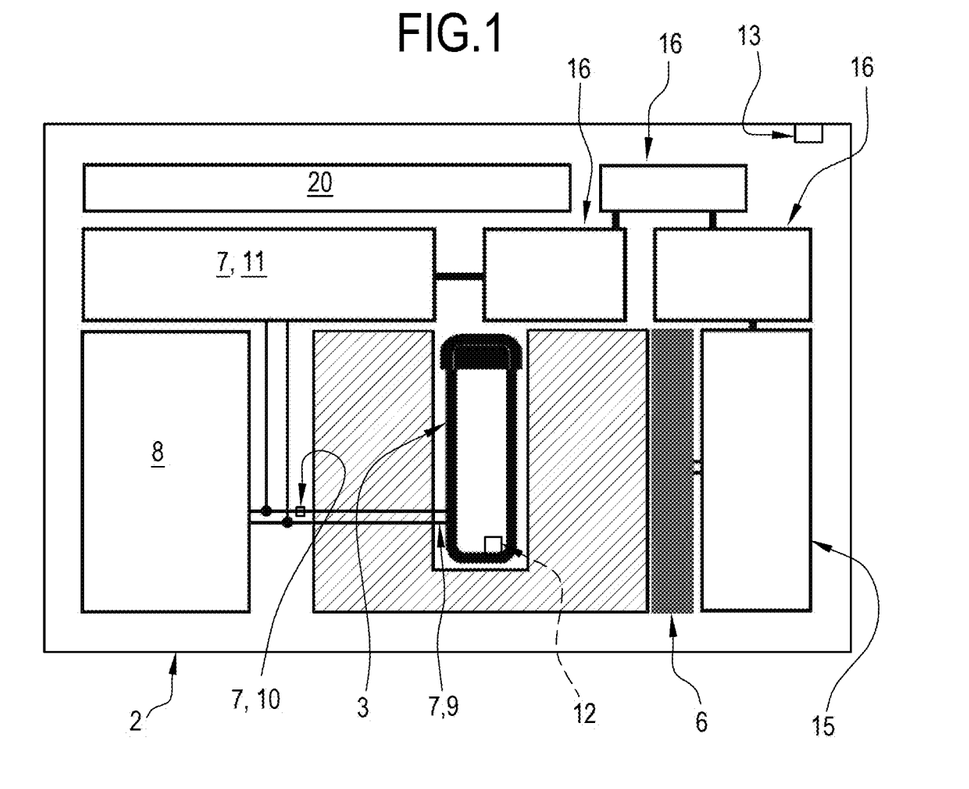
FIGS. 1 and 2 are respective schematic views of an embodiment of the apparatus and method for determining the bacterial charge in a liquid or semi-liquid product according to the invention.
Figure 2:
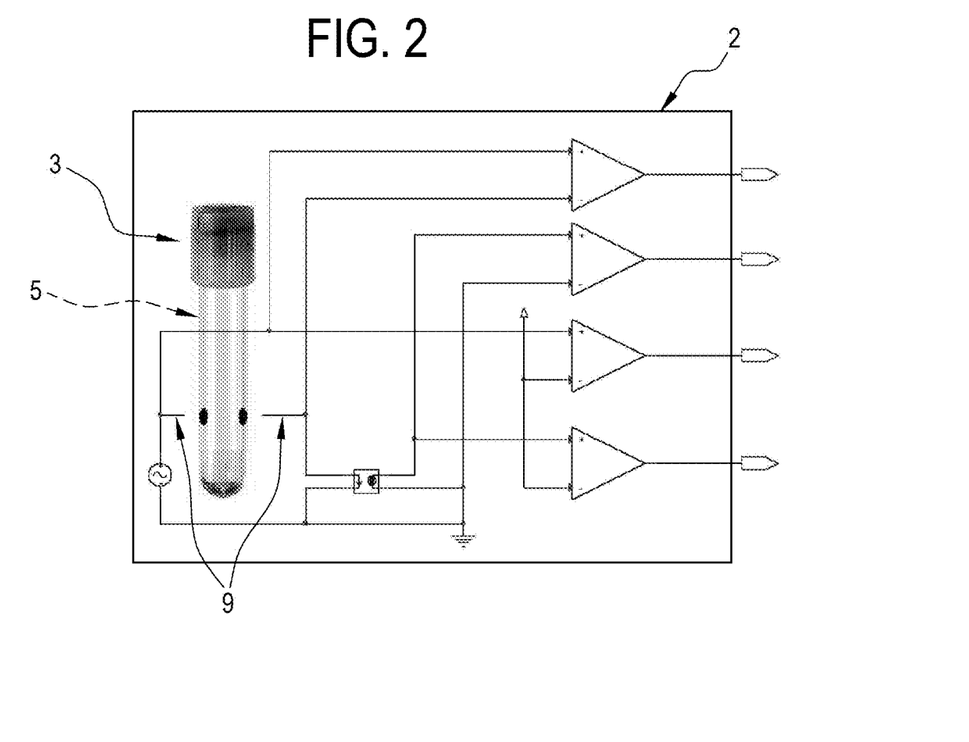

Preferably, the apparatus 1 for measuring the bacterial charge in a liquid or semi-liquid product comprises:

a supporting frame 2;

a container 3 which is removable from the supporting frame 2 and whose internal containing space 5 is adapted to be filled with a liquid or semi-liquid product to be tested;

heating means 6 (or heater, preferably electrical) associated with the supporting frame 2 and, in use, in thermal contact with the removable container 3 to heat the liquid or semi-liquid product to be tested;

a control unit 15 configured to control the heating means 6 in such a way as to keep the liquid or semi-liquid product at a predetermined measuring temperature ($T_m$);

an electronic measuring unit 7 comprising:

a signal generator 8 (electronic) adapted to generate an electrical voltage signal Vref which is variable over time;

measuring electrodes 9 electrically connected to the signal generator 8 and mounted inside the internal containing space 5 of the removable container 3;

a sensor 10 adapted to measure a current (Iout) flowing through the measuring electrodes 9 and the liquid or semi-liquid product consequent upon the electrical voltage signal Vref;

a calculator unit 11 configured to calculate, based on the current Iout measured by the sensor 10 and based on the electrical voltage signal Vref, a value α representing an angle of electrical impedance of the liquid or semi-liquid product at predetermined instants and corresponding to a time phase shift between the current Iout and the electrical voltage signal Vref.

It should be noted, therefore, that the electronic measuring unit 7 is configured to derive an indication of the bacterial charge concentration based on the time trend of the values a representing an angle of electrical impedance of the liquid or semi-liquid product being tested (acquired at different instants of time).

Preferably, the removable container 3 is a test tube.

Preferably, the removable container 3 comprises a containing portion for containing the liquid or semi-liquid product and a lid.

Preferably, the control unit 15 is associated with (housed in) the supporting frame 2 and includes an electronic processor and predetermined programming.

Preferably, the electronic measuring unit 7 is associated with (housed in) the supporting frame 2.

It should be noted that the sensor 10 adapted to measure a current Iout flowing through the measuring electrodes 9 and the liquid or semi-liquid product consequent upon the electrical voltage signal Vref may be a sensor of any kind (voltage sensor, current sensor, etc.).

In effect, as is known, current can be measured in any of a plurality of different ways using any of a plurality of sensors.

According to one aspect, the apparatus 1 comprises a first temperature sensor 12 associated, in use, with the removable container 3, to measure the temperature of the liquid or semi-liquid product, and the control unit 15 is configured to control the heating means 6 (that is, the preferably electrical heater) as a function of the temperature measured by the first temperature sensor 12.

Preferably, the control unit 15 is configured to control the heating means 6 in closed loop (by feedback) based on the temperature measured by the first temperature sensor 12 and a reference temperature $T_m$.

The reference temperature $T_m$ corresponds to a reference temperature for feedback control (the control unit 15 configured to control the heating means 6 in such a way as to keep the liquid or semi-liquid product at a predetermined reference temperature $T_m$, plus or minus a certain tolerance).

It should be noted that the reference temperature preferably corresponds to a temperature in the range between 30° C. and 45° C., and still more preferably between 35° C. and 40° C.

According to another aspect, the apparatus 1 further comprises a second temperature sensor 13 for measuring the ambient temperature, and the control unit 15 is configured to control the heating means 6 also as a function of the ambient temperature measured by the second temperature sensor 13.

Control based also on measurement of the ambient temperature makes it possible to prevent measurement of product temperature inside the container 3 from being affected (altered) by sudden changes in temperature (especially positive ones, that is, due to external heat sources).

In effect, knowing the ambient temperature allows optimal control of the heating means 6, in particular by controlling their thermal power.

According to one aspect, the heating means 6 are configured to release a variable thermal power and the control unit 15 regulates the thermal power released by the heating means 6.

According to another aspect, the control unit 15 and the electronic measuring unit 7 are (electronically) independent of each other.

According to another aspect, the apparatus 1 further comprises a bus and the control unit 15 and electronic measuring unit 7 are connected to the bus 16.

Preferably, the control unit 15 and the electronic measuring unit 7 are configured as "slave" units.

The bus 16 is preferably a modbus.

Figure 4:
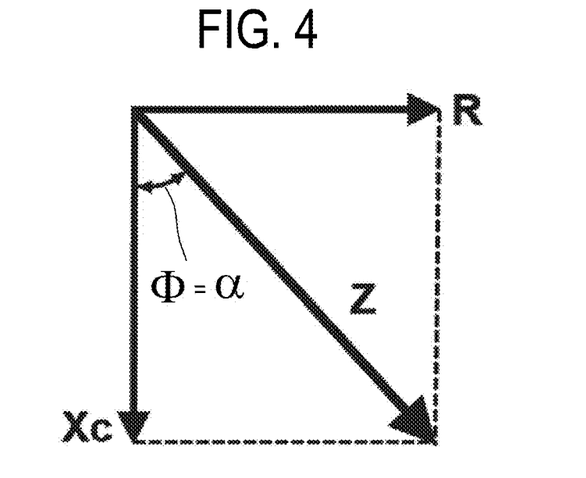
FIG. 4 is an impedance diagram showing the reactive impedance Xc, the resistive impedance R and the impedance angle ϕ.

According to another aspect, the calculator unit 11 is configured to derive the value α representing the angle of impedance according to the following formula:

$\alpha = T_0 - T_1$, where $T_0$ is the time instant in which the electrical voltage signal Vref is zero (with positive or negative derivative) and $T_1$ is the time instant in which the current Iout is zero (with positive or negative derivative, and in any case having the same sign as the derivative of the electrical signal Vref used to calculate $T_0$).

It should be noted that the calculator unit 11 preferably comprises a device (a timer, that is, a periodic signal generator) adapted to generate a time signal which can be used to identify the instants $T_0$ and $T_1$ in the time domain.

Figure 3:
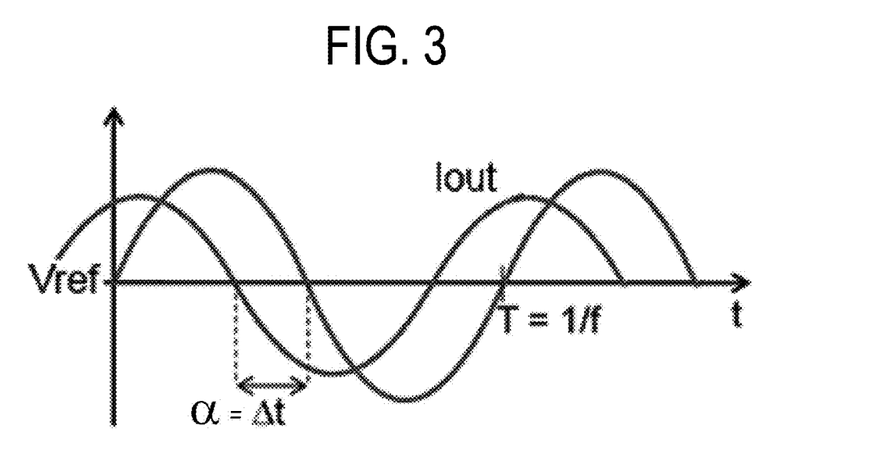
FIG. 3 is a graph schematically representing the voltage applied and the resulting current measured in a liquid or semi-liquid product tested in a container of the apparatus of the preceding figures.

FIG. 3 illustrates this aspect.

It should be noted that the fact of deriving a value α representing the angle of electrical impedance of the liquid or semi-liquid product through a time measurement of $T_0$ and $T_1$ followed by a difference operation advantageously means that this value can be derived with considerable accuracy and precision; in effect, electronic devices (e.g. microprocessors) can be used to measure the times with a high degree of precision.

Thus, measuring a value α representing the angle of electrical impedance of the liquid or semi-liquid product is particularly fast and reliable.

The heating means 6 preferably comprise a Peltier cell.

Preferably, the apparatus 1 comprises a power supply 20 connectable to the electrical mains and adapted to power one or more of the electrical devices or units described above.

According to another aspect, the apparatus 1 may comprise a battery (not illustrated).

According to another aspect, as illustrated in FIG. 3, the electrical signal (Vref) is a sinusoidal signal.

According to another aspect, the signal is a periodic signal with a frequency of between 150 and 300 Hz.

Still more preferably, the frequency is between 180 Hz and 220 Hz.

Figure 5:
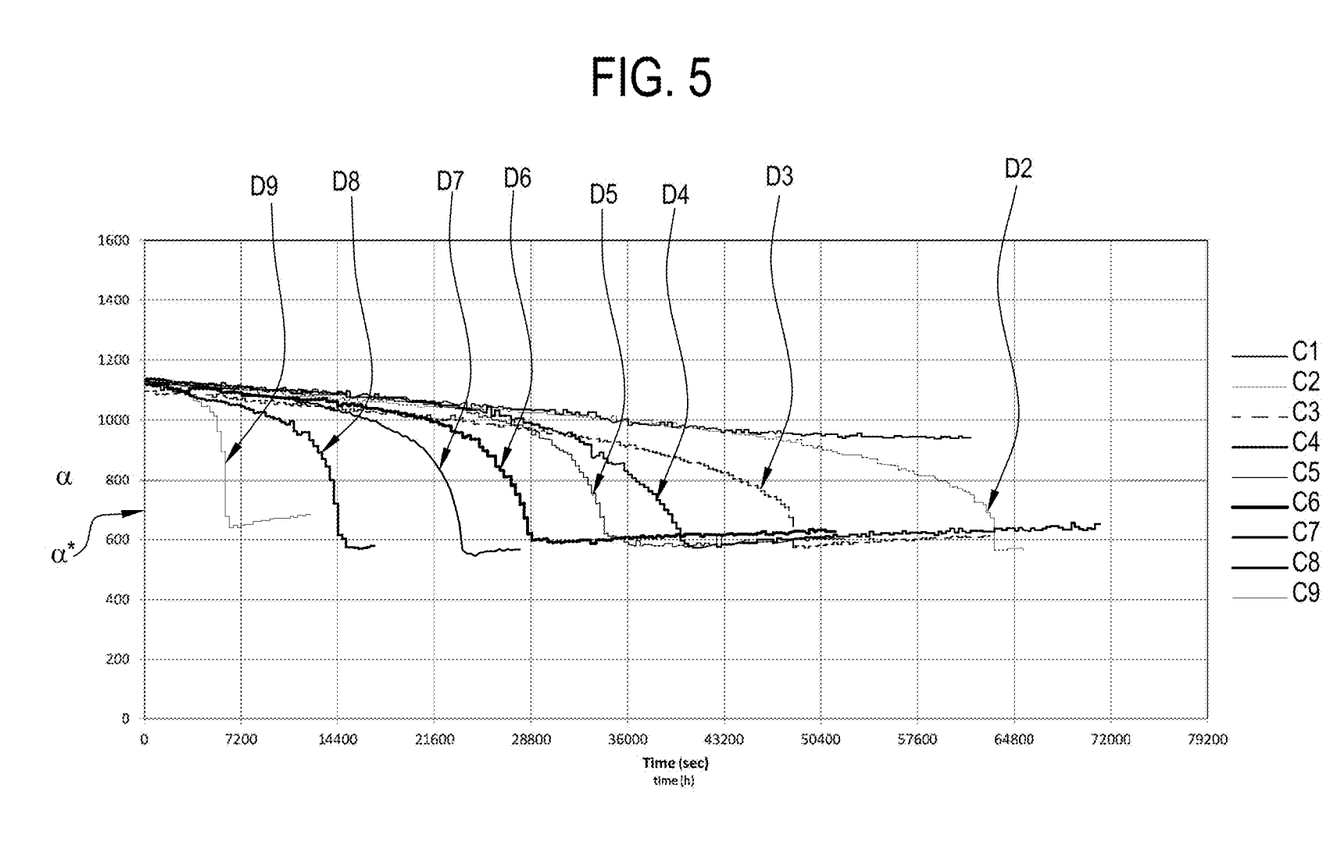
FIG. 5 schematically represents the impedance angle (axis of ordinates) over time (axis of abscissas) for a plurality of test samples with different bacterial charges.

The graph of FIG. 5 shows the value α (on the axis of ordinates) representing the angle of electrical impedance of the liquid or semi-liquid product as a function of time (axis of abscissas), for different values of initial bacterial charges (C1=absence of bacteria, C2, C3, C4, C5, C6, C7, C8, C9, C10).

The graph of FIG. 5 is the result of an experimental test carried out for different values of bacterial charge concentration.

In the graph, C1=absence of bacteria, C2=10 cfu/ml, C3=10^2 cfu/ml, C4=5*10^2 cfu/ml, C5=7.5*10^2 cfu/ml, C6=3*10^4 cfu/ml, C7=2*10^5 cfu/ml, C8=5*10^7 cfu/ml, C9=10^10 cfu/ml.

According to another aspect, the calculator unit 11 is configured for:

calculating a time derivative of the values a representing the angle of electrical impedance of the liquid or semi-liquid product at successive time instants;

for each time instant, comparing the derivative with a predetermined reference value to check whether that derivative is greater than the predetermined reference value;

if the derivative is greater than the predetermined reference value for one of the time instants, calculating a value of bacterial charge concentration corresponding to that time instant using a predetermined relation between bacterial charge concentration and measuring time.

It should be noted that the "measuring time" is the time between the time instant at which measuring starts and the instant at which the derivative becomes greater than the predetermined reference value for one of these time instants.

According to one aspect, the derivative is a first derivative.

According to one aspect, the derivative is a second derivative.

The reference labels D2, D3, D4, D5, D6, D7, D8, D9 in FIG. 5 denote possible reference derivative values (for different test concentrations).

Preferably, the reference derivative value is a high value: thus, the measurement of the bacterial charge concentration is considerably more reliable.

In effect, this makes it possible to determine the time instant (that is, in which measuring time) the derivative of the value α exceeds a predetermined high value, that is, when the signal of the value α undergoes a sudden change of derivative (first or second).

As shown in FIG. 5, this time instant is clearly identifiable if the reference derivative value is a high value (as in the case of D2, D3, D4, D5, D6, D7, D8, D9).

Figure 6:
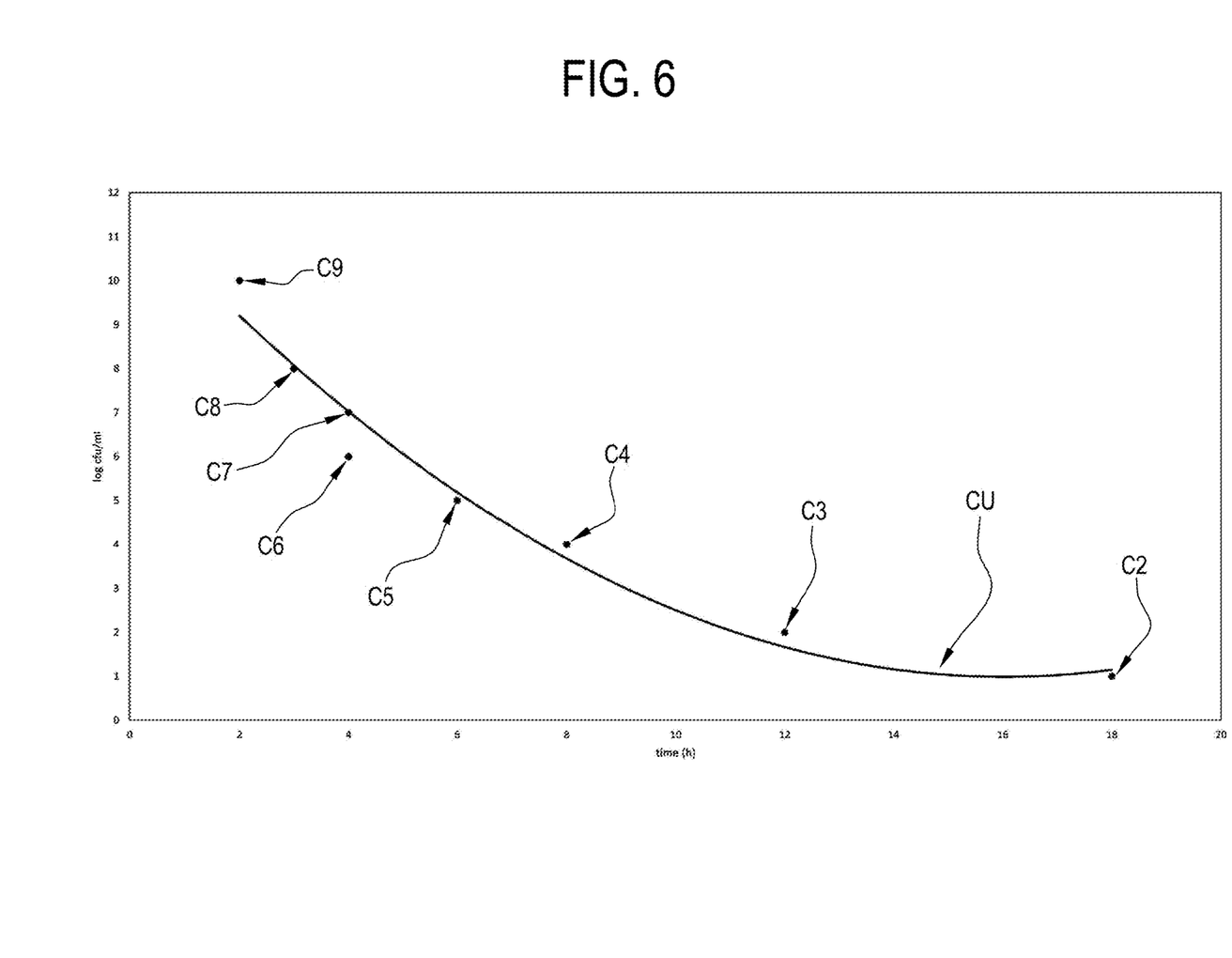
FIG. 6 represents some bacterial charge concentration values (axis of ordinates) and the relates times (axis of abscissas), extracted from some of the test samples of FIG. 5.

FIG. 6 shows the bacterial charge concentration derived for the test samples of FIG. 5 (with the exception of C1).

It should be noted that FIG. 6 shows a curve CU of second order interpolating the values shown (C2-C9).

According to another aspect, the calculator unit 11 is configured for:

for each time instant, comparing the value α representing an angle of the electrical impedance with a predetermined reference value to check whether the value α representing a derived angle of the electrical impedance is greater than the predetermined reference value;

if the value α representing a derived angle of the electrical impedance is greater than the predetermined reference value, calculating a value of bacterial charge concentration corresponding to that time instant using a predetermined relation between measuring time and bacterial charge concentration.

According to this aspect, the concentration value is not derived or calculated using the derivative but using the value α representing an angle of the electrical impedance.

As shown in FIG. 5, for each test bacterial charge concentration (C2-C9), the value α representing an angle of the electrical impedance tends to an asymptotic value α* after a certain length of time.

Measuring this measuring length of time, that is the time in which the value α representing an angle of the electrical impedance tends to an asymptotic value α* (that is, reaches a value greater than α* by a predetermined tolerance Delta α), allows deriving an indication of the bacterial charge concentration in the liquid or semi-liquid product being tested.

Another aspect defines a method for determining the bacterial charge in a liquid or semi-liquid product, comprising:

preparing a quantity of liquid or semi-liquid product to be analyzed;

keeping that quantity of liquid or semi-liquid product at a preset measuring temperature ($T_m$) and deriving values a representing an angle of electrical impedance of the liquid or semi-liquid product at predetermined time instants;

deriving a bacterial charge concentration in the liquid or semi-liquid product as a function of the time trend of the values a representing an angle of electrical impedance.

According to another aspect of the method, the step of deriving values of angle α of electrical impedance comprises a step of generating a time-variable electrical voltage signal Vref in the liquid or semi-liquid product and a step of measuring, in the liquid or semi-liquid product, an electrical current Iout due to the electrical voltage signal Vref.

According to yet another aspect, the variable electrical voltage signal Vref is a signal which is periodic (over time).

According to yet another aspect, the step of deriving a value α representing an angle of electrical impedance of the liquid or semi-liquid product at successive time instants comprises the following steps, for each time instant:

detecting the time instant $T_0$ in which the electrical voltage signal Vref is zero;

detecting the time instant $T_1$ in which the current signal Iout due to the electrical voltage signal Vref is zero;

calculating the value α of the angle of electrical impedance of the liquid or semi-liquid product at that time instant according to the following formula:

$\alpha = T_0 - T_1$, where $T_0$ is the time instant in which the electrical voltage signal Vref is zero and $T_1$ is the time instant in which the current Iout is zero.

According to another aspect, the electrical voltage signal has a frequency of between 100 Hz and 500 Hz (more preferably, between 150 Hz and 300 Hz).

According to another aspect, the step of deriving values a representing an angle of electrical impedance of the liquid or semi-liquid product at predetermined time instants comprises the following steps:

a step of measuring the temperature of the liquid or semi-liquid product to be analyzed; and a step of heating the liquid or semi-liquid product to be analyzed in order to keep it at a preset measuring temperature $T_m$ based on the temperature signal of the liquid or semi-liquid product.

Preferably, the step of keeping the quantity of liquid or semi-liquid product at a preset measuring temperature $T_m$ and deriving values a representing an angle of electrical impedance of the liquid or semi-liquid product at predetermined time instants also comprises a step of measuring the external ambient temperature and wherein the step of heating the liquid or semi-liquid product to be analyzed in order to keep it at a preset measuring temperature $T_m$ based on the temperature signal of the liquid or semi-liquid product comprises heating the liquid or semi-liquid product at a preset measuring temperature $T_m$ based on the temperature signal of the liquid or semi-liquid product and also on the external ambient temperature signal.

According to another aspect of the method, the step of keeping the quantity of liquid or semi-liquid product at a preset measuring temperature (Tm) comprises a step of heating the quantity of liquid or semi-liquid product using a Peltier cell.

According to another aspect of the method, the step of deriving an indication of the presence of a bacterial charge in the liquid or semi-liquid product as a function of the time trend of the values a representing the angle of the electrical impedance comprises the following steps:

calculating a time derivative of the values a of the angle of electrical impedance of the liquid or semi-liquid product at successive time instants;

for each time instant of the successive time instants, comparing the derivative with a predetermined reference value to check whether that derivative is greater than the predetermined reference value;

if the derivative is greater than the predetermined reference value for one of the time instants, calculating, for that time instant, a value of bacterial charge concentration corresponding to that time instant (or measuring time) using a predetermined relation between bacterial charge concentration and time.

According to another aspect of the method, the derivative is a first derivative.

According to another aspect of the method, the derivative is a second derivative.

According to another aspect, the step of deriving an indication of the presence of a bacterial charge in the liquid or semi-liquid product as a function of the time trend of the values a representing the angle of the electrical impedance comprises the following steps:

for each time instant, comparing the value α representing an angle of the electrical impedance with a predetermined reference value to check whether the value α representing a derived angle of the electrical impedance is greater than the predetermined reference value;

if the value α representing a derived angle of the electrical impedance is greater than the predetermined reference value, calculating, for that time instant, a value of bacterial charge concentration corresponding to that time instant using a predetermined relation between bacterial charge concentration and (measuring) time.

According to another aspect, the time trend of the values (α) representing the angle of the electrical impedance is a time-decreasing function (as shown in FIG. 5, where time is represented on the axis of abscissas and a value representing the electrical impedance angle measured is represented on the axis of ordinates).

The unit of measure of the axis of ordinates in the graph of FIG. 5 is the radian, multiplied by 1000.

The unit of measure of the axis of abscissas in the graph of FIG. 5 is the hour (measuring time).

According to another aspect, the relation between bacterial charge concentration and measuring time is a function in which the bacterial charge concentration is decreasing relative to the measuring time (as shown in FIG. 6, where the measuring time is represented on the axis of abscissas and bacterial charge concentration is represented on the axis of ordinates).

According to one aspect, the relation between bacterial charge concentration and measuring time is a function of second order, or of second degree in the measuring time (as shown in FIG. 6, where the relation between the bacterial charge concentration and the measuring time is in the form $y=a*t^2+b*t+c$, where y is the bacterial charge concentration in the liquid or semi-liquid product, t is the measuring time and a, b and c are numerical values).

According to another aspect, the aforementioned relation between bacterial charge concentration and time is, with reference to the bacterial charge concentration, a function of the exponential measuring time with positive base less than 1 and with positive (measuring time) exponent.

According to yet another aspect, the aforementioned relation between bacterial charge concentration and time is, with reference to the bacterial charge concentration, is a function of the exponential measuring time with positive base less than 1 and with positive time exponent.

According to another aspect, the aforementioned relation between bacterial charge concentration and measuring time is, with reference to the bacterial charge concentration, a linear time function with a negative angular coefficient.

According to another aspect, the method comprises a step of deriving a predetermined number of values (e.g. a number "n") representing an angle of electrical impedance of the liquid or semi-liquid product at predetermined time instants and then performing the following operations.

This predetermined number of values is used to construct an interpolating curve (preferably polynomial) of degree (n−1), that is, having as degree the predetermined number of values minus one unit).

Preferably, the degree of the interpolating curve is greater than 5 and less than 15.

The derivatives (preferably first derivatives) for each of the "n" values representing an angle of electrical impedance are calculated on this interpolating curve representing an angle of electrical impedance.

If present, the value (or "detection time point") representing an angle of electrical impedance whose derivative is higher than a preset threshold (threshold value) is identified from among the (first) derivatives for each of the "n" values representing an angle of electrical impedance.

The derivative may be calculated with a preceding or succeeding point.

It should be noted that when a new value representing an angle of electrical impedance of the liquid or semi-liquid product is derived, another interpolating curve is calculated, based on the n−1 values representing an angle of electrical impedance excluding the first of the values representing an angle of electrical impedance and including the new value representing an angle of electrical impedance of the liquid or semi-liquid product.

It should be noted that this method allows implementing a sort of window which moves with each new value representing an angle of electrical impedance of the liquid or semi-liquid product and which always contains (n−1) points.

What is claimed is:

1. A method for determining a bacterial charge in a liquid or semi-liquid product, comprising:
   providing:
      a supporting frame;
      a container which is removable from the supporting frame and including an internal containing space suitable for being filled with a liquid or semi-liquid product to be tested;
      a heater connected to the supporting frame and, in use, in thermal contact with the container to heat the liquid or semi-liquid product to be tested;
      a control unit configured to control the heater to keep the liquid or semi-liquid product at a predetermined measuring temperature ($T_m$), the control unit including an electronic processor and predetermined programming;
      an electronic measuring unit comprising:
      a signal generator adapted to generate an electrical voltage signal (Vref) which is variable over time;
      measuring electrodes electrically connected to the signal generator and mounted inside the internal containing space of the removable container;
      a sensor adapted to measure a current (Iout) flowing through the measuring electrodes and the liquid or semi-liquid product consequent upon the electrical voltage signal (Vref);
      a calculator unit configured to calculate, based on the current (Iout) measured by the sensor and based on the electrical voltage signal (Vref), values (α) representing an angle of electrical impedance of the liquid or semi-liquid product at predetermined time instants and corresponding to a time phase shift between the current (Iout) and the electrical voltage signal (Vref);
   wherein the calculator unit is configured for:
      calculating a time derivative of the values (α) at successive time instants;
      for each of the successive time instants, comparing the time derivative with a predetermined reference value to check whether the time derivative is greater than the predetermined reference value;
      if the time derivative is greater than the predetermined reference value for one of the successive time instants, calculating a value of bacterial charge concentration corresponding to the one of the successive time instants using a predetermined relation between bacterial charge concentration and time;
   preparing a quantity of liquid or semi-liquid product to be tested;
   keeping the quantity of liquid or semi-liquid product at the predetermined measuring temperature ($T_m$) and calculating the time derivatives of the values (α);

deriving a bacterial charge concentration in the liquid or semi-liquid product as a function of a time trend of the values ($\alpha$).

2. The method according to claim 1, wherein the step of deriving the values ($\alpha$) comprises a step of generating the time-variable electrical voltage signal (Vref) in the liquid or semi-liquid product and a step of measuring, in the liquid or semi-liquid product, the electrical current (Iout) due to the electrical voltage signal (Vref).

3. The method according to claim 1, wherein the step of deriving the value ($\alpha$) of the angle of electrical impedance of the liquid or semi-liquid product at successive time instants comprises the following steps, for each time instant:
   detecting a time instant ($T_0$) in which the electrical voltage signal (Vref) is zero;
   detecting a time instant ($T_1$) in which the current signal (Iout) due to the electrical voltage signal (Vref) is zero;
   calculating the value ($\alpha$) of the angle of electrical impedance of the liquid or semi-liquid product at that time instant according to the following formula:
   $\alpha = T_0 - T_1$, where $T_0$ is the time instant in which the electrical voltage signal (Vref) is zero and $T_1$ is the time instant in which the current (Iout) is zero.

4. The method according to claim 1, wherein the step of deriving values ($\alpha$) representing an angle of electrical impedance of the liquid or semi-liquid product at predetermined time instants comprises the following steps:
   a step of measuring a temperature of the liquid or semi-liquid product to be analyzed; and
   a step of heating the liquid or semi-liquid product to be analyzed in order to keep the liquid or semi-liquid product at the predetermined measuring temperature ($T_m$) based on a temperature signal of the liquid or semi-liquid product.

5. The method according to claim 4, wherein the step of keeping the quantity of liquid or semi-liquid product at the predetermined measuring temperature ($T_m$) and deriving values ($\alpha$) representing an angle of electrical impedance of the liquid or semi-liquid product at successive time instants also comprises a step of measuring the external ambient temperature and wherein the step of heating the liquid or semi-liquid product to be analyzed in order to keep it at the predetermined measuring temperature ($T_m$) based on the temperature signal of the liquid or semi-liquid product comprises heating the liquid or semi-liquid product at the predetermined measuring temperature ($T_m$) based on the temperature signal of the liquid or semi-liquid product and also on an external ambient temperature signal.

6. The method according to claim 1, wherein the step of deriving a bacterial charge concentration in the liquid or semi-liquid product as a function of the time trend of the values ($\alpha$) representing the angle of electrical impedance comprises the following steps:
   for each time instant, comparing the value ($\alpha$) representing an angle of the electrical impedance with a predetermined reference value to check whether the value ($\alpha$) representing a derived angle of the electrical impedance is greater than the predetermined reference value;
   if the value ($\alpha$) representing a derived angle of the electrical impedance is greater than the predetermined reference value, calculating, for that time instant, a value of bacterial charge concentration corresponding to that time instant using a predetermined relation between bacterial charge concentration and time.

7. The method according to claim 6, wherein the relation between bacterial charge concentration and time is a function in which the bacterial charge concentration is decreasing relative to the time.

8. The method according to claim 7, wherein the predetermined concentration relation is a second order function.

9. The method according to claim 7, wherein the predetermined relation between bacterial charge concentration and measuring time is, with reference to the bacterial charge concentration, an exponential time function with positive base less than 1 and with positive measuring time exponent.

10. An apparatus for measuring a bacterial charge in a liquid or semi-liquid product, comprising:
    a supporting frame;
    a container which is removable from the supporting frame and including an internal containing space suitable for being filled with a liquid or semi-liquid product to be tested;
    a heater connected to the supporting frame and, in use, in thermal contact with the container to heat the liquid or semi-liquid product to be tested;
    a control unit configured to control the heater to keep the liquid or semi-liquid product at a predetermined measuring temperature ($T_m$), the control unit including an electronic processor and predetermined programming;
    an electronic measuring unit comprising:
      a signal generator adapted to generate an electrical voltage signal (Vref) which is variable over time;
      measuring electrodes electrically connected to the signal generator and mounted inside the internal containing space of the removable container;
      a sensor adapted to measure a current (Iout) flowing through the measuring electrodes and the liquid or semi-liquid product consequent upon the electrical voltage signal (Vref);
      a calculator unit configured to calculate, based on the current (Iout) measured by the sensor and based on the electrical voltage signal (Vref), values ($\alpha$) representing an angle of electrical impedance of the liquid or semi-liquid product at predetermined time instants and corresponding to a time phase shift between the current (Iout) and the electrical voltage signal (Vref);
    wherein the calculator unit is configured for:
      calculating a time derivative of the values ($\alpha$) at successive time instants;
      for each of the successive time instants, comparing the time derivative with a predetermined reference value to check whether the time derivative is greater than the predetermined reference value;
      if the time derivative is greater than the predetermined reference value for one of the successive time instants, calculating a value of bacterial charge concentration corresponding to the one of the successive time instants using a predetermined relation between bacterial charge concentration and time.

11. The apparatus according to claim 10, further comprising a first temperature sensor operatively connected, in use, with the removable container, to measure a temperature of the liquid or semi-liquid product, and wherein the control unit is configured to control the heater as a function of the temperature measured by the first temperature sensor.

12. The apparatus according to claim 11, further comprising a second temperature sensor for measuring an ambient temperature and wherein the control unit is configured to control the heater as a function of the ambient temperature measured by the second temperature sensor.

13. The apparatus according to claim 10, wherein the time derivative is a first derivative.

14. The apparatus according to claim 10, wherein the time derivative is a second derivative.

15. An apparatus for measuring a bacterial charge in a liquid or semi-liquid product, comprising:
   a supporting frame;
   a container which is removable from the supporting frame and including an internal containing space suitable for being filled with a liquid or semi-liquid product to be tested;
   a heater connected to the supporting frame and, in use, in thermal contact with the container to heat the liquid or semi-liquid product to be tested;
   a control unit configured to control the heater to keep the liquid or semi-liquid product at a predetermined measuring temperature ($T_m$), the control unit including an electronic processor and predetermined programming;
   an electronic measuring unit comprising:
      a signal generator adapted to generate an electrical voltage signal (Vref) which is variable over time;
      measuring electrodes electrically connected to the signal generator and mounted inside the internal containing space of the removable container;
      a sensor adapted to measure a current (Iout) flowing through the measuring electrodes and the liquid or semi-liquid product consequent upon the electrical voltage signal (Vref);
      a calculator unit configured to calculate, based on the current (Iout) measured by the sensor and based on the electrical voltage signal (Vref), values ($\alpha$) representing an angle of electrical impedance of the liquid or semi-liquid product at predetermined time instants and corresponding to a time phase shift between the current (Iout) and the electrical voltage signal (Vref);
      wherein the calculator unit is configured for:
         comparing, for each time instant, the value ($\alpha$) representing a derived angle of the electrical impedance with a predetermined reference value to check whether the value ($\alpha$) representing a derived angle of the electrical impedance is greater than the predetermined reference value;
         if the value ($\alpha$) representing a derived angle of the electrical impedance is greater than the predetermined reference value, calculating a value of bacterial charge concentration corresponding to that time instant using a predetermined relation between time and bacterial charge concentration.

16. An apparatus for measuring a bacterial charge in a liquid or semi-liquid product, comprising:
   a supporting frame;
   a container which is removable from the supporting frame and including an internal containing space suitable for being filled with a liquid or semi-liquid product to be tested;
   a heater connected to the supporting frame and, in use, in thermal contact with the container to heat the liquid or semi-liquid product to be tested;
   a control unit configured to control the heater to keep the liquid or semi-liquid product at a predetermined measuring temperature ($T_m$), the control unit including an electronic processor and predetermined programming;
   an electronic measuring unit comprising:
      a signal generator adapted to generate an electrical voltage signal (Vref) which is variable over time;
      measuring electrodes electrically connected to the signal generator and mounted inside the internal containing space of the removable container;
      a sensor adapted to measure a current (Iout) flowing through the measuring electrodes and the liquid or semi-liquid product consequent upon the electrical voltage signal (Vref);
      a calculator unit configured to calculate, based on the current (Iout) measured by the sensor and based on the electrical voltage signal (Vref), values ($\alpha$) representing an angle of electrical impedance of the liquid or semi-liquid product at predetermined time instants and corresponding to a time phase shift between the current (Iout) and the electrical voltage signal (Vref);
      wherein the calculator unit is configured to derive, for each time instant, the value ($\alpha$) according to the following formula:
         $\alpha = T_0 - T_1$, where $T_0$ is the time instant in which the electrical voltage signal (Vref) is zero and $T_1$ is the time instant in which the current (Iout) is zero.

* * * * *